(12) United States Patent
Chen et al.

(10) Patent No.: US 6,433,176 B1
(45) Date of Patent: Aug. 13, 2002

(54) METHOD FOR MAKING 8-HYDROXYJULOLIDINE COMPOUND

(75) Inventors: Chao-Tsen Chen; Shao-Tzu Tang; Ling Lu; Jim-Min Fang, all of Taipei (TW)

(73) Assignee: Allied Industrial Corp., Ltd., Taipei (TW)

( * ) Notice: Subject to any disclaimer, the term of this patent is extended or adjusted under 35 U.S.C. 154(b) by 0 days.

(21) Appl. No.: 09/793,627

(22) Filed: Feb. 27, 2001

(51) Int. Cl.[7] ............................................. C07D 455/04
(52) U.S. Cl. ......................................................... 546/94
(58) Field of Search .......................................... 546/94

(56) References Cited

U.S. PATENT DOCUMENTS 4,005,092 A * 1/1977 Reynlds .................. 260/287 P
4,471,441 A * 9/1984 Baranyl et al. ............... 430/89

* cited by examiner

*Primary Examiner*—Patricia L. Morris
(74) *Attorney, Agent, or Firm*—Bacon & Thomas

(57) ABSTRACT

An 8-hydroxyjulolidine compound, having the formula:

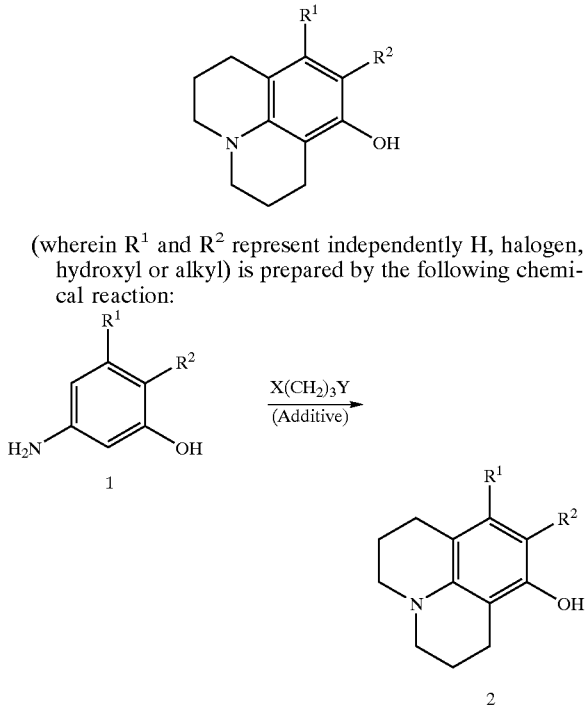

(wherein $R^1$ and $R^2$ represent independently H, halogen, hydroxyl or alkyl) is prepared by the following chemical reaction:

wherein X and Y represent independently halogen, acyloxyl, sulfonyloxyl or phosphoryloxyl and $R^1$ and $R^2$ are as defined above.

11 Claims, No Drawings

METHOD FOR MAKING 8-HYDROXYJULOLIDINE COMPOUND

FIELD OF INVENTION

The present invention relates to 8-hydroxyjulolidine and its analogous compounds and preparation thereof, especially to a one-step cyclization reaction of 3-aminophenol or 1,3-dihydroxyaniline with 1,3-dihalopropane or its analogs to prepare the desired julolidines. The 8-hydroxyjulolidine and its analogous compounds have the following chemical structure:

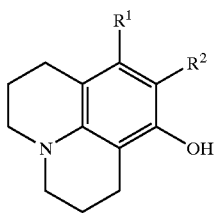

2 wherein $R^1$ and $R^2$ represent independently hydrogen, halogen, hydroxyl group or alkyl groups.

BACKGROUND OF INVENTION

Coumarins are often used as lasing dyes and fluorescent probes in bioassays, because they exhibit the beneficial properties of tunable wavelengths, high quantum yields, high absorption coefficient and little overlapping in the absorption and emission spectra. According to U.S. Pat. No. 3,873,940, U.S. Pat. No. 3,932,415, U.S. Pat. No. 4,005,092, U.S. Pat. No. 4,471,041, U.S. Pat. No. 4,736,032 and U.S. Pat. No. 4,794,184, coumarin compounds with fused and rigid nitrogen-containing rings significantly hinder the mobility of amino groups and thus reduce the energy dissipation caused by the rotation of uncyclized amino groups. Such rigid coumarins also greatly increase the dipolar moments in the excited states, and thus attain high quantum yields and emission efficiencies in lasing.

However, there are only a few methods for the preparation of 8-hydroxyjulolidine and 8,10-dihydroxyjulolidine have been disclosed. In the conventional art, method for the preparation of these compounds, such as those disclosed in U.S. Pat. No. 4,005,092, U.S. Pat. No. 4,471,041 and *Journal of Organic Chemistry* (1987) Vol. 52, pp. 1465–1468, 8-hydroxyjulolidine and 8,10-dihydroxyjulolidine are prepared by cyclization of m-anisidine (or 3,5-dimethoxyaniline) with excess amounts of 1-bromo-3-chloropropane, followed by demethylation with strong acids. Using dimethyl sulfate for methylations of 3-aminophenol and 3,5-dihydroxyaniline is generally carried out to obtain m-anisidine and 3,5-dimethoxyaniline.

The above-mentioned methods have several disadvantages. First, in the mass production of 8-hydroxyjulolidine or 8,10-dihydroxyjulolidine, excess 1-bromo-3-chloropropane (7.6–15 molar proportions) is used. Such an approach will bring out relatively higher production costs. Secondly, in the step of demethylation corrosive strong acids such as hydrochloric acid, hydroiodic acid and boron tribromide are needed. These materials are hazardous to the environment. Thirdly, the overall yields in the above-said approaches are low (<30%) due to the need of two extra steps, prior protection of the hydroxyl group with a toxic reagent of dimethyl sulfate and removal of the protecting methyl group after the cyclization reaction.

It is thus necessary to provide a novel method for the preparation of 8-hydroxyjulolidine and its analogous compounds wherein preparation costs may be reduced.

It is also necessary to provide a method for the preparation of 8-hydroxyjulolidine and its analogous compounds wherein no hazardous material is needed.

It is also necessary to provide a method for the preparation of 8-hydroxyjulolidine and its analogous compounds wherein yields of preparation may be improved.

It is also necessary to provide a simplified method for the preparation of 8-hydroxyjulolidine and its analogous compounds.

OBJECTIVES OF INVENTION

The objective of this invention is to provide a simplified method for the preparation of 8-hydroxyjulolidine and its analogous compounds wherein only one single step reaction is needed.

Another objective of this invention is to provide a novel method for the preparation of 8-hydroxyjulolidine and its analogous compounds wherein preparation costs may be reduced.

Another objective of this invention is to provide a method for the preparation of 8-hydroxyjulolidine and its analogous compounds wherein no hazardous material is needed.

Another objective of this invention is to provide a method for the preparation of 8-hydroxyjulolidine and its analogous compounds wherein yields of preparation may be improved.

SUMMARY OF INVENTION

According to this invention, a novel method for the preparation of 8-hydroxyjulolidine and its analogous compounds is disclosed. In the invented method, desired julolidines may be easily prepared by a single-step cyclization reaction, without the need of steps such as prior protection of hydroxyl groups or removal of the methyl groups. The invented method discloses an alkylative cyclization reaction at the amino group of the reactant whereby the hydroxyl group of the reactant will not be affected. As a result, yield of the invented method may be higher than that of the conventional method. The invented method comprises the following chemical reactions:

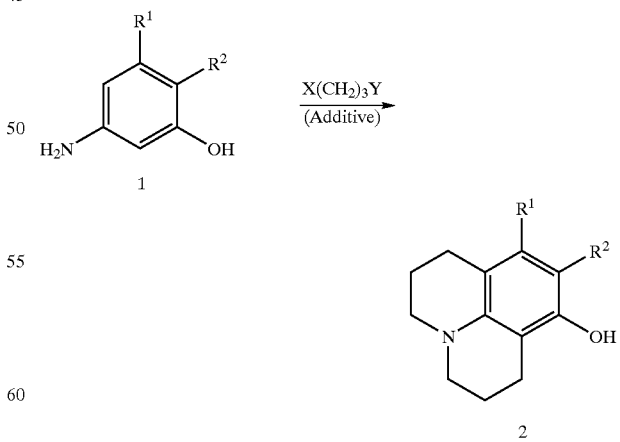

wherein X and Y represent independently halogen, acyloxyl, sulfonyloxyl or phosphoryloxyl group, and $R^1$ and $R^2$ represent independently H, halogen, hydroxyl, or alkyl group. In the reaction solution, an organic alkali, an inorganic alkali or a phase-transfer agent may be added. Suitable additives include triethylamine, LiOH, $Na_2CO_3$, $NaHCO_3$, organic ammonium salts and organic sulfonates.

The products of this invention have the following structure:

$$\text{(structure 2: julolidine with } R^1, R^2, \text{ and OH substituents)}$$

wherein $R^1$ and $R^2$ are defined as above.

The invented method comprises a cyclization reaction of 3-aminophenol or 1,3-dihydroxyaniline with 1,3-dihalopropane or its analogs.

This invention also discloses a method of recrystallization or a solid-liquid continuous extraction of 8-hydroxyjulolidine and its analogous compounds to obtain purified products.

This invention also discloses a method for the preparation of various coumarins by further treatment of the resulting 8-hydroxyjulolidine and its analogs with appropriate reagents such as malonate and acetoacetate. This invention also discloses the products and intermediates prepared therefrom.

DETAILED DESCRIPTION OF INVENTION

In order to illustrate the features and advantages of this invention, the following embodiments are given as examples.

EMBODIMENT 1

SYNTHESIS OF 8-HYDROXYJULOLIDINE m-Aminophenol (110 mg, 1 mmol), 1-bromo-3-chloropropane (2.35 g, 1.6 ml, 15 mmol) and anhydrous $Na_2CO_3$ (212 g, 2 mmol) were placed in a 100 ml two-necked round-bottomed flask equipped with a thermometer and an addition funnel containing molecular sieves (4 Å, 0.3 g). The top of the funnel was fitted with a condenser. Under an atmosphere of nitrogen, the mixture was heated to 70° C. for 3 hours and then refluxed at 110° C. for 15 hours. The resulting red mixture was cooled to room temperature and concentrated HCl solution (15 ml) was slowly added with care. After addition of $CH_2Cl_2$ (5 ml), the aqueous layer was separated. The aqueous phase was neutralized by the addition of 40% NaOH aqueous solution and extracted with $CH_2Cl_2$ (50 ml×4). The $CH_2Cl_2$ extracts were combined, washed with brine, dried over anhydrous $MgSO_4$ and concentrated in reduced pressure. The crude product was subjected to silica gel column chromatography by elution with EtOAc/hexane (1:9) to give pure compound of 8-hydroxyjulolidine (72 mg, 0.38 mmol) in 38% yield.

Colorless crystals were obtained by recrystallization from hexane. M.p.: 128–130° C. (literature value 126–128° C.). TLC (EtOAc/hexane, 1:9) $R_f$=0.23. $^1H$ NMR ($CDCl_3$, 300 MHz): δ 1.94–1.99 (4 H, m), 2.62–2.70 (4 H, m), 3.04–3.12 (4 H, m), 4.43 (1 H, s), 6.04 (1 H, d, J=7.9 Hz), 6.64 (1 H, d, J=7.9 Hz).

EMBODIMENT 2

SYNTHESIS OF 8-HYDROXYJULOLIDINE

According to a procedure similar to that of Embodiment 1, a mixture of m-aminophenol (1.1 g, 10 mmol), 1-bromo-3-chloropropane (23.5 g, 16 ml, 150 mmol) and anhydrous $Na_2CO_3$ (4.27 g, 40 mmol) was heated and stirred at 70° C. for 3 hours and refluxed at 110° C. for 15 hours. After silica gel column chromatography, 8-hydroxyjulolidine (800 mg) was obtained in 42% yield.

EMBODIMENT 3

SYNTHESIS OF 8-HYDROXYJULOLIDINE

According to a procedure similar to that of Embodiment 1, a mixture of m-aminophenol (11.0 g, 101 mmol), 1-bromo-3-chloropropane (127.4 g, 80 ml, 809 mmol) and anhydrous $Na_2CO_3$ (42.4 g, 400 mmol) was heated and stirred at 70° C. for 3 hours and refluxed at 110° C. for 15 hours. After silica gel column chromatography, 8-hydroxyjulolidine (7.3 g) was obtained in 38% yield.

EMBODIMENT 4

SYNTHESIS OF 8-HYDROXYJULOLIDINE

According to a procedure similar to that of Embodiment 1, a mixture of m-aminophenol (5.0 g, 46 mmol), 1-bromo-3-chloropropane (23.9 g, 15 ml, 151 mmol) and N,N-dimethylformamide (15 ml) was heated and refluxed for 15 hours. After silica gel column chromatography, 8-hydroxyjulolidine (5.5 g) was obtained in 62% yield.

EXAMPLE 5

SYNTHESIS OF 8-HYDROXYJULOLIDINE m-Aminophenol (1.1 g, 10 mmol), 1-bromo-3-chloropropane (4.8 g, 3 ml, 30 mmol) and ethanol (10 ml) were placed in a 100 ml two-necked round-bottomed flask. The mixture was heated and refluxed for 11 hours, during which an $NaHCO_3$ aqueous solution (2.0 g, 20 ml, 23 mmol) was added. The mixture was further heated and refluxed for 37 hours. The solvent was removed by distillation under reduced pressure. The resulting crude product was extracted with hexane by a solid-liquid continuous extraction to give 8-hydroxyjulolidine (661 mg) in 35% yield.

EMBODIMENT 6

SYNTHESIS OF 8-HYDROXYJULOLIDINE

According to a procedure similar to that of Embodiment 5, a mixture of m-aminophenol (5.0 g, 45.8 mmol), 1-bromo-3-chloropropane (23.9 g, 15 ml, 150 mmol) and ethanol (50 ml) was heated and refluxed. $NaHCO_3$ (10.0 g, 119 mmol) aqueous solution (20 ml) was added slowly. After 24 hours of reflux, 3.4 g of 8-hydroxyjulolidine was obtained in 39% yield.

EMBODIMENT 7

SYNTHESIS OF 8-HYDROXYJULOLIDINE

According to a procedure similar to that of Embodiment 1, a mixture of m-aminophenol (110 mg, 1 mmol), 1-bromo-3-chloropropane (0.48 g, 0.3 ml, 3 mmol), sodium dihydrogen phosphate dihydrate ($NaH_2PO_4·2H_2O$, 623 mg, 4 mmol) and water (10 ml) was heated and refluxed for 12 hours. After silica gel column chromatography, 8-hydroxyjulolidine (30 mg) was obtained in 16% yield.

EMBODIMENT 8

SYNTHESIS OF 8-HYDROXYJULOLIDINE

According to a procedure similar to that of Embodiment 1, a mixture of m-aminophenol (115 mg, 1 mmol), 1-bromo- 3-chloropropane (0.48 g, 0.3 ml, 3 mmol) and a buffer solution prepared by dissolving 1.50 g (4 mmol) of disodium hydrogen phosphate decahydrate ($Na_2HPO_4,12H_2O$) and 0.60 g (4 mmol) of $NaH_2PO_4 2H_2O$ in 10 ml water was heated and refluxed for 24 hours. After silica gel column chromatography, 8-hydroxyjulolidine (40 mg) was obtained in 21% yield.

EMBODIMENT 9

SYNTHESIS OF 8-HYDROXYJULOLIDINE

According to a procedure similar to that of Embodiment 1, a mixture of m-aminophenol (116 mg, 1 mmol), 1-bromo-3-chloropropane (0.48 g, 0.3 ml, 3 mmol), dodecylbenzenesulfonic acid sodium salt (349 mg, 1 mmol) and a buffer solution prepared by dissolving 1.50 g (4 mmol) of $Na_2HPO_4 12H_2O$ and 0.60 g (4 mmol) of $NaH_2PO_4 2H_2O$ in water (10 ml) was heated and refluxed for 12 hours. After silica gel column chromatography, 8-hydroxyjulolidine (28 mg) was obtained in 15% yield.

EMBODIMENT 10

SYNTHESIS OF 8-HYDROXYJULOLIDINE

According to a procedure similar to that of Embodiment 1, a mixture of m-aminophenol (110 mg, 1 mmol), 1,3-bis(toluenesulfonyloxy)propane (3.84 g, 10 mmol), wet 1,4-dioxane (3 ml) and anhydrous $Na_2CO_3$ (424 mg, 4 mmol) was heated and refluxed for 5 days. After silica gel column chromatography, 8-hydroxyjulolidine (51 mg) was obtained in 27% yield.

EMBODIMENT 11

SYNTHESIS OF 8,10-DIHYDROXYJULOLIDINE

According to a procedure similar to that of Embodiment 1, a mixture of 3,5dihydroxyaniline(1.30 g, 10 mmol), 1-bromo-3chloropropane (4.77 g, 3 ml, 30 mmol) and N,N-dimethylformamide (10 ml) was heated and refluxed for 5 hours. After silica gel column chromatography, 8,10-dihydroxyjulolidine (617 mg) was obtained in 30% yield. The product is not stable and will turn from colorless to red when exposed to air.

M.p.: 164–168° C. TLC (EtOAc/hexane, 1:2). $R_f$=0.34. $^1H$ NMR ($CDCl_3$, 300 MHz): δ1.87 (4 H, m), 2.51 (4 H, m), 2.94 (4 H, m), 5.63 (1 H, s). $^{13}C$ NMR 15 ($CDCl_3/CD_3OD$, 100 MHz): δ 20.6 (2×), 21.9 (2×), 50.1 (2×), 91.4, 100.8 (2×),144.6, 152.3(2×). IR(KBr): 2932,2846, 1593, 1434, 1288, 1142, 1089 $cm^{-1}$. MS (FAB): m/z 205 ($M^+$).

EMBODIMENT 12

SYNTHESIS OF 8,10-DIBENZOYLOXYJULOLIDINE AND 8,10-DIHYDROXYJULOLIDINE

A mixture of 3,5-(dibenzoyloxy)aniline(3.5 g, 11.3 mmol), 1-bromo-3-chloropropane (12.7 g, 9.2 ml, 84.5 mmol), triethylamine (3.5 g, 4.7 ml, 33.3 mmol) and dioxane (45 ml) was heated and refluxed at 96–100° C. for 24 hours. Volatiles were removed and the resulting product was extracted with $CH_2Cl_2$ (30 ml) and rinsed by a saturated $NaHCO_3$ aqueous water solution (15 ml). The resulting aqueous phase was extracted with $CH_2Cl_2$ (15 ml×2). The $CH_2Cl_2$ extracts were combined, concentrated, and added ethyl acetate to force sedimentation. The sediments were removed by filtration. The remaining filtrate solution was concentrated and subjected to silica gel column chromatography by elution with EtOAc/hexane.

The resulting product is recrystallized from EtOAc/hexane to give light yellow crystals of 8,10-dibenzoyloxyjulolidine (1.2 g, 3.1 mmol) in 28% yield.

M.p. 84–86° C. TLC (EtOAc/hexane, 1:9). $R_f$=0.44. $^1H$ NMR ($CDCl_3$, 300 MHz): δ 1.90–1.98 (4 H, quint, j=6 Hz), 2.70 (4 H, t, j=6 Hz), 3.06 (4 H, t, J=6 Hz), 4.99 (4 H s), 5.98 (1 H, s), 7.20–7.41(10H, m). $^{13}C$ NMR ($CDCl_3$, 100 MHz): δ 21.13 (2×), 21.91 (2×), 50.14 (2×), 70.04 (2×), 87.45, 103.71 (2×), 127.08 (4×), 127.50 (2×),128.45 (4×), 137.87 (2×), 144.56, 154.98 (2×). IR(KBr): 2919, 2853, 1600, 1493, 1454, 1281, 1169 $cm^{-1}$. MS: m/z385 ($M^+$), 294 ($M-Bn^+$), 91 ($Bn^+$).

In a solution of 8,10-dibenzoyloxyjulolidine (1.2 g, 3.1 mmol) in ethyl acetate (60 ml), a 10% palladium catalyst on charcoal support is added. The solution is covered by hydrogen balloon and stirred for 6 hours. The solution is filtered, concentrated and subjected to silica gel column chromatography to give 520 mg of 8,10-dihydroxyjulolidine in 81% yield.

EXAMPLE 13

SYNTHESIS OF 8,10-DIHYDROXY-9-FORMYLJULOLIDINE AND THE SUBSEQUENT CONDENSATION WITH DIETHYL MALONATE

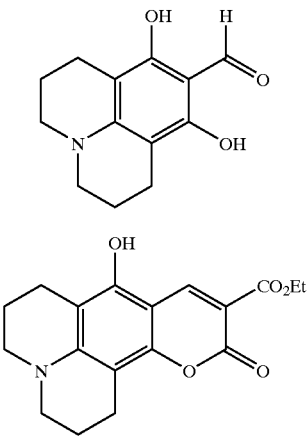

A mixture of 8,10-dihydroxyjulolidine (1.00 g, 5 mmol), N,N-dimethylformamide (1 ml) and a mixture of phosphoryl chloride ($POCl_3$, 790 mg, 0.5 ml, 5.6 mmol) in N,N-dimethylformamide (5 ml) was stirred at room temperature for 1 hour. Water (1 ml) was added, the resulting precipitates were filtered, and the filtrate was concentrated to give 8,10-dihydroxy-9- formyljulolidine (formula 3 above, 932 mg) in 80% yield. $^1H$ NMR ($CDCl_3$, 200 M)"δ 1.82 (4 H, m), 2.47 (4 H, m), 3.16 (4 H, m), 9.70 (1 H, s).

A mixture of 8,10-dihydroxy-9-formyljulolidine (232 mg, 0.9 mmol), diethyl malonate (114 mg, 0.1 ml, 1 mmol) and piperidine (172 mg, 0.2 ml, 2 mmol) in acetonitrile ($CH_3CN$, 1 ml) and benzene (3 ml) was heated and refluxed for 2 hours. The solvents were removed under reduced pressure, and the crude product was purified by recrystallization with ethyl acetate to give the coumarin compound (formula 4 above, 293 mg) in 89% yield. $^1HNMR$ ($CDCl_3$, 300 MHz): δ 1.36(3 H, t, J=6.0 Hz), 1.93 (4 H, m), 2.61 (2 H, t, J=6.4 Hz), 2.77(2 H, t, J=6.4 Hz), 3.28(4 H, m), 4.33 (2 H, q,J=6.0 Hz), 8.75 (1 H, s).

EXAMPLE 14

CONDENSATION OF 8,10-DIHYDROXYJULOLIDINE AND ETHYL ACETOACETATE

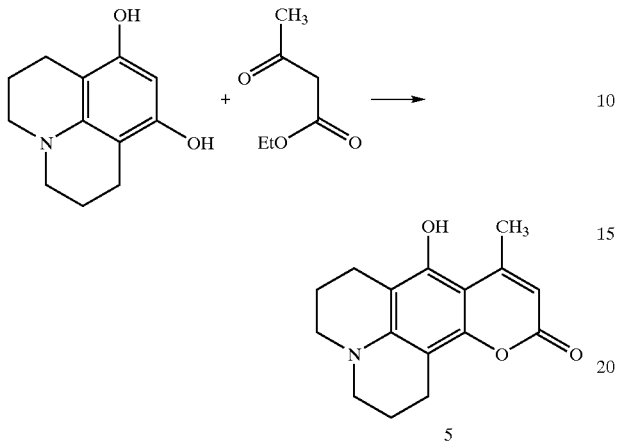

5

A mixture of 8,10-dihydroxyjulolidine (208 mg, 1 mmol), ethyl acetoacetate (220 mg, 16 mmol), zinc chloride (ZnCl$_2$, 12 mg, 1.2 mmol) and ethanol(10 ml) was heated and refluxed for 22 hours. The solvents were removed under reduced pressure, and the crude product was purified by recrystallization with ethyl acetate to give the coumarin compound(formula 5 above, 225 mg) in 83% yield. $^1$H NMR (CDCl$_3$, 200 MHz): δ 1.90 (4 H, m),2.49 (3 H, s), 2.53 (4 H, m), 3.23 (4 H, m), 5.67 (1 H, s).

EXAMPLE 15

SYNTHESIS OF THE 4-CYANO SUBSTITUTED COUMARIN

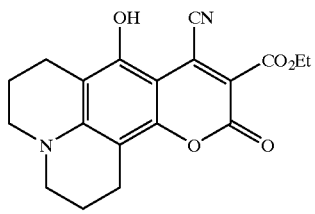

6

A suspension of a coumarin of (formula 5 as shown in Embodiment 13, 520 mg, 1.66 mmol) in N,N-dimethylformamide (10 ml) was added a 30% sodium cyanide (163 mg, 3.32 mmol) aqueous solution(0.4 ml) at room temperature. The mixture was stirred and cooled in an ice bath. Bromine (292 mg, 1.83 mmol) was added dropwise with care. The mixture turned from orange color to pink color, and precipitates were formed. The mixture was stirred at room temperature for 16 hours. The precipitates were filtered and rinsed with small amounts of N,N-dimethylformamide and water. The filtrate was extracted with ethyl acetate (60 ml×3). The extract was concentrated and the remaining crude product was purified by recrystallization to give the coumarin compound (formula 6 above, 540 mg) in 96% yield.

M.p. 175–177° C. TLC(EtOAc/hexane, 1:1). R$_f$=0.24. $^1$HNMR (CDCl$_3$,200 MHz): δ 1.39 (3 H, t, J=7 Hz), 1.94–1.96 (4 H, m), 2.74–2.84 (4 H, m), 3.31–3.39 (4 H m), 4.40(2H, q, J=7 Hz), 7.24(1 H, s). $^{13}$C NMR(CDCl$_3$, 50MHz): δ 14.0, 19.9, 20.9, 27.4, 50.0, 50.4, 62.2, 106.0, 106.5, 110.2, 113.2, 120.7, 124.8, 127.4, 149.2, 152.0, 157.0, 162.7.IR (KBr): 2335, 1748, 1614 cm$^{-1}$. MS: m/z 338 (M$^+$), 310(M$^+$–CO), 266 (M+–CO$_2$C$_2$H$_5$), 57 (C$_3$H$_7$N$^+$). UV-vis: $\lambda_{max}$=508.8 nm (ε=27478) in EtOH; 503.6 nm(ε=31236) in acetone; 494.4 nm (ε=21726) in THF. Fluorescence: $\lambda_{max}$=560 nm in EtOAc; 559 nm in THF; 569 nm in acetone; 575 nm in EtOH. Anal. calcd for C$_{19}$H$_{18}$N$_2$O$_4$: C, 67.44; H, 5.36; N, 8.27. Found: C, 67.15; H, 5.36; N, 8.17.

As the present invention has been shown and described with reference to preferred embodiments thereof, those skilled in the art will recognize that the above and other changes may be made therein without departing form the spirit and scope of the invention.

What is claimed is:

1. A method for the preparation of a 8-hydroxyjulolidine having the following chemical structure:

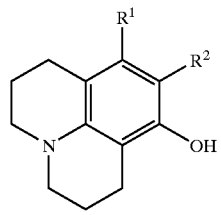

2 wherein R$^1$ and R$^2$ represent independently H, halogen, hydroxyl or alkyl group; said method comprising the following chemical reaction:

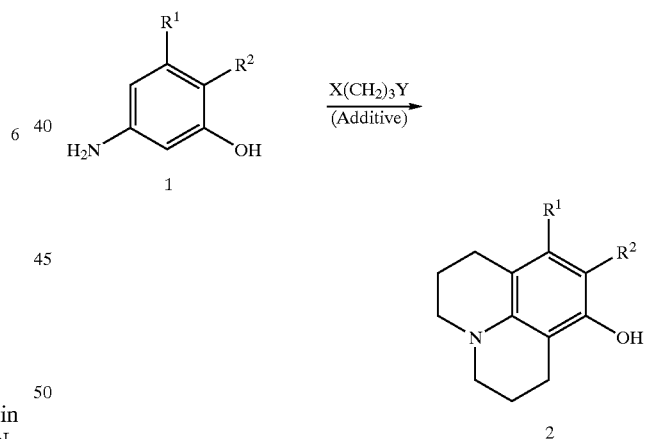

wherein X and Y represent independently halogen, acyloxyl, sulfonyloxyl or phosphoryloxyl group, and R$^1$ and R$^2$ are as defined above.

2. The method according to claim 1 wherein said chemical reaction is conducted under the existence of a solvent selected from the group consisted of water, benzenes, ethers, alcohols, nitrites, amides or their combination.

3. The method according to claim 1 wherein the molar ratio of compound X(CH$_2$)$_3$Y to aminophenol compound (formula 1) is in the range of 0.1 to 100.

4. The method according to claim 1 wherein said chemical reaction is conducted under the existence of an additive selected from the group consisted of organic base or inorganic alkali.

5. The method according to claim 1 wherein said additive is an organic base selected from the group consisted of cyclic amine and acyclic amine.

6. The method according to claim 1 wherein said additive is an inorganic alkali selected from the group consisted of hydroxide, carbonate, bicarbonate, phosphate, hydrogen phosphate, and dihydrogen phosphate.

7. The method according to claim 1 wherein said chemical reaction is conducted under the existence of a phase-transfer agent.

8. The method according to claim 7 wherein said phase-transfer agent is selected from the group consisted of organic ammonium salt or organic sulfonate.

9. The method according to claim 1 wherein said acyloxyl group is an alkanoyloxy or benzoyloxy group.

10. The method according to claim 1, further comprising a step of purifying the product by solid-liquid continuous extraction or recrystallization.

11. The method according to claim 10 wherein solvent for said recrystallization is selected from the group consisted of alkane, haloalkane, benzene, ether, ester and their combination.

* * * * *